United States Patent [19]
Goldberg et al.

[11] Patent Number: 5,306,489
[45] Date of Patent: * Apr. 26, 1994

[54] HAIR CARE PRODUCTS CONTAINING N-ALKOXYALKYLAMIDES

[75] Inventors: Marvin E. Goldberg, Marlboro; Malti Bhambhani, Scotch Plains, both of N.J.; Arthur Brandon, Valley Cottage, N.Y.

[73] Assignee: Revlon Consumer Products Corporation, New York, N.Y.

[*] Notice: The portion of the term of this patent subsequent to Jan. 28, 2009 has been disclaimed.

[21] Appl. No.: 920,220

[22] Filed: Jul. 24, 1992

[51] Int. Cl.$^5$ .......................... A61K 7/11; A61K 7/06
[52] U.S. Cl. ........................................ 424/71; 424/70; 424/47; 424/DIG. 2
[58] Field of Search ........................ 424/70, 71, 47, 60; 514/625

[56] References Cited

U.S. PATENT DOCUMENTS

| 3,230,228 | 1/1966 | Erlemann | 260/295 |
|---|---|---|---|
| 3,322,635 | 5/1967 | Erlemann | 514/629 |
| 3,984,566 | 10/1976 | Van Scott | 424/283 |
| 4,021,572 | 5/1977 | Van Scott | 424/317 |
| 4,105,782 | 4/1978 | Yu | 424/283 |
| 4,105,783 | 4/1978 | Yu | 424/283 |
| 4,197,316 | 0/1980 | Yu | 424/317 |
| 4,234,599 | 11/1980 | Van Scott | 424/279 |
| 4,334,097 | 6/1982 | Schmidt | 564/201 |
| 4,382,765 | 5/1983 | Moller | 424/365 |
| 4,614,748 | 9/1986 | Taya | 514/613 |
| 4,973,473 | 11/1990 | Schneider | 514/847 |
| 5,051,251 | 9/1991 | Morita et al. | 424/70 |
| 5,084,270 | 1/1992 | Ciaudelli | 424/59 |

FOREIGN PATENT DOCUMENTS 2321752 4/1973 Fed. Rep. of Germany .
2338087 7/1973 Fed. Rep. of Germany .
2632391 7/1976 Fed. Rep. of Germany .

OTHER PUBLICATIONS

Chemical Abstracts, vol. 33, No. 18, Sep. 20, 1939.
Chemical Abstracts, vol. 63, No. 9, Oct. 25, 1965.

Primary Examiner—Thurman K. Page
Assistant Examiner—Sally Gardner
Attorney, Agent, or Firm—Julie Blackburn

[57] ABSTRACT

A hair care composition comprising N-alkoxyalkylamides of the formula:

$$OH-CH_2-(CHOH)_p-\overset{O}{\overset{\|}{C}}-\overset{H}{\overset{|}{N}}-(C_nH_{2n})-O-(C_mH_{2m+1})$$

wherein p is a whole number from 1 to about 4,
(C$_n$H$_{2n}$) is a straight or branched chain alkyl bridge in which n is a whole number of 1 to about 6, and is preferably 3,
(C$_m$H$_{2m+1}$) is a straight or branched chain alkyl radical in which m is a whole number of 1 to about 6 and is preferably 1.

15 Claims, 4 Drawing Sheets

HAIR CARE PRODUCTS CONTAINING N-ALKOXYALKYLAMIDES

TECHNICAL FIELD

The invention relates to hair care compositions such as shampoo, hair conditioner, hair spray, and hair setting and styling compositions containing N-alkoxyalkylamides.

BACKGROUND OF THE INVENTION

Hair shampoos contain as active ingredients anionic detergents which foam and clean hair. While very effective in their function of cleansing, anionics can be harsh to the hair surface, leaving hair in an overly dry, unmanageable state. Furthermore, the hair is rendered susceptible to electrostatic charge accumulation which promulgates the undesireable condition known as fly away hair. To mollify these adverse effects, it is the usual practice to incorporate selective ingredients into the shampoo formulation, other than those which contribute to product aesthetics. These selective mollifying additives, while effective in providing greater manageability and hair conditioning, unfortunately interfere with and reduce the anionic detergent's effectiveness in cleansing and foaming.

Hair conditioners and creme rinse preparations, on the other hand, employ cationic surfactants as their key ingredients. There materials, usually quaternary ammonium compounds, are substantive to the negatively charged keratinaceous protein of hair. Because of their substantive properties, treatment of hair with a hair conditioner containing cationic quaternary ammonium compounds (generally after shampooing) provides the hair with a lubricating surface film which allows for easy combing. Hence, knots and tangles, encountered in hair combing after shampooing, are easily dissipated through hair treatment with a cationic hair conditioner. Notwithstanding their desirable characteristics, cationic hair conditioners formulated with quaternary ammonium compounds tend to overcondition the hair, making the hair undesirably heavy, "bodiless" and unattractive in appearance.

Hair setting lotions and hair sprays are usually based upon polymeric resins which provide hair fixative effects. Hair is given rigidity through application of these products enabling the hair to hold a style configuration in place. Plasticizers are also formulated into the product which provide pliability to the films of the polymeric resin coating the hair. The plasticizers allow the resin film to bend, instead of rupturing or breaking under the stress of slight hair movement. However, the total hair holding potential of the polymeric hair fixative is reduced when plasticizers are incorporated. As a result, the strength of the hair configuration is weakened and the hair style is shortlived.

We have now discovered that a small amount of a specific N-alkyoxyalkylamide, when incorporated with the key ingredients of a shampoo, cationic hair conditioner, or resinous hair fixative product provide a product with a unique feel, lubricity, and sheen, without being greasy or heavy. In addition, treated hair is smoother, and easier to manage, has increased body, fullness, and softness. The N-alkyoxyamides of the invention are compatible with anionic surfactants, cationic surfactants, and polymeric resins in their respective formulation environment.

SUMMARY OF THE INVENTION

The invention is directed to a hair care composition comprising a compound of the formula (Formula I):

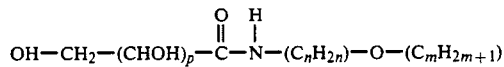

wherein p is a whole number from 1 to about 4,
$(C_nH_{2n})$ is a straight or branched chain alkyl bridge in which n is a whole number of 1 to about 6, and is preferably 3,
$(C_mH_{2m+1})$ is a straight or branched chain alkyl radical in which m is a whole number of 1 to about 6 and is preferably 1.

DETAILED DESCRIPTION

Figure 1:
FIG. 1: is a photograph at 5000X magnification of a brown hair tress which was shampooed ten times with a standard shampoo composition containing 5% methoxypropylgluconamide. The brown hair tress shows build up of material on and between the cuticle layers of the tress.

The preferred hair care composition of the invention contains a compound of the formula (Formula II):

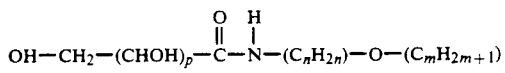

wherein
p is a whole number from 1 to 4,
($C_nH_{2n}$) is a straight or branched chain alkyl bridge in which n is a whole number of 1 to 4, and is preferably 3, and
($C_mH_{2m+1}$) is a straight or branched chain alkyl radical in which m is a whole number of 1 to 4, and is preferably 1.

The most preferred compound of Formula II above is wherein p is 4, n is 3, and m is 1. This compound is methyoxy propyl gluconamide (hereinafter "MPG") as has the following formula (Formula III):

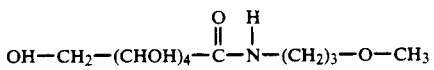

The term "hair care composition" means, in accordance with the invention, a shampoo, hairspray, gel, conditioner, mousse, or the like.

It is suggested that the hair care composition of the invention contain about 0.001–10% of the Formula I, II, or III compounds, with 0.005–7% preferred and 0.005–5% preferred.

When the compounds of the invention are incorporated into shampoos, the resulting shampoo provides excellent lubricity, sheen, and manageability to hair without any greasy or heavy feel. The hair is also smoother and easier to manage, and has improved body, fullness, and softness. Generally suitable shampoo formulations comprise 1–45% anionic surfactant, and about 1–55% water. Additionally the shampoo may contain foam boosters, thickeners, chelating agents, preservatives, etc.

If foam boosters are added, generally 0.01–10% is suggested. Suitable foam boosters include cocamide MEA, cocamide DEA, lauramide DEA, capramide DEA, cetearyl alcohol, cetyl alcohol, cetyl betaine, cocamide MIPA, cocamidoethyl betaine, cocamidopropylamine oxide, cocamidopropyl betaine, cocamidopropyl hydroxysultaine, cocamide oxide, coconut alcohol, coco-sultaine, lauryl betaine, lauryl sultaine, lauryl alcohol, myristamide DEA, myristamide MEA, oleyl betaine, sodium sarcosinates, postassium coco hydrolyzed silk protein etc. are suitable.

A great variety of thickeners are suitable including cellulose derivatives such as hydroxyethyl cellulose, hydroxypropyl cellulose, $C_{9-15}$ alcohols, Carbomers, guar gum, magnesium silicate, as well as various acrylic acid derivatives, PEG monostearates, etc. A range of 0.01–10% is suggested.

Generally about 0.001–1% preservative is suggested. The suitable preservatives are those used traditionally in shampoo or other hair care compositions.

It may be also desired to add a chelating agent which is capable of complexing with and inactivating metal ions to prevent adverse effects to the formulation. Generally about 0.001–1% chelating agent is suggested. Suitable chelating agents are EDTA, HEDTA, TEA-EDTA, sodium metasilicate, sodium metaphosphate, sodium citrate, or mixtures thereof.

The compounds of Formula I, II, and III also provide excellent properties to hair when added to hair conditioning compositions. Generally, about 0.001–10% of the compounds of the invention will suffice, with 0.005–7% preferred and 0.005–5% most preferred.

Suitable conditioning compositions comprise about 1.0–10% of a cationic polymer, 10–95% water, and 0.1–10% of a conditioning agent. Suitable cationic polymers include cationic quaternary ammonium compounds such as cetyl trimethyl ammonium chloride, cetrimonium chloride, stearylamidopropyl ethyldimonium ethosulfate, Polyquat 11, oleylamidopropyl amine oxide, guar hydroxypropyl trimonium chloride, trimethylsilylamodimethicone, stearyl dimethyl benzyl ammonium chloride, cetyl pyridinium chloride, dicetyl dimethyl ammonium chloride, or mixtures thereof.

Suitable conditioning agents include cetyl alcohol, hydrolyzed collagen, stearamidopropyl dimethyl amine, wheat germ oil, silk protein, keratin amino acids, cocdimonium silk amino acids, panthenol, dimethicone, dimethicone copolyol, or mixtures thereof.

The conditioning agents may also contain emulsifiers, thickeners, acidulants, preservatives, fragrances, etc.

Emulsifiers are generally desireable and include ethoxylated cetyl/stearyl alcohol, cetearyl alcohol, etc. About 0.01–5% emulsifier is suggested.

Thickeners are also desireable and include cellulose derivatives, PPG-Buteth derivatives, etc. Generally 0.01–5% thickener is suggested.

Acidulants may be added to keep the pH of the conditioner in the range of 2.5–6.0 Suitable acidulants are L citric acid and the like, generally in a range of 0.001–1%.

The compounds of Formula I, II, and III also provide sheen, lubricity and softness to hair when used in hair sprays or hair fixative compositions. The Formula I, II, and III compounds are generally added in amounts of 0.001–10%, with 0.005–7% preferred and 0.005–5% most preferred.

A suitable hair spray composition comprises 0.5–10% resin, 0.001–5% resins, 0.01–5% neutralizers, 0.01–5% plasticizers and about 15–40% solvent and, if desired, 5–60% propellant.

Suitable resins include vinyl acetate/crotonic acid/vinyl neodecanoate copolymer, octyl acrylamide/acrylates/butyl amino ethyl methacrylate copolymer, vinyl acetate/crotonic acid, polyvinylpyrollidone, polyvinyl pyrollidone vinyl acetate copolymer, PVP acrylates copolymer, the ethyl ester of polyvinyl methylether/maleic anhydride, polyvinylpyrrolidone acetate, polymeric quaternary ammonium salts prepared by the reaction of ethyl methacrylate/abietylmethacrylate/diethylamino ethyl methacrylate copolymer with dimethyl sulfate, a polymeric quaternary ammonium salt prepared by the reaction of ethyl methacrylate/oleylmethacrylate/diethylamino ethyl methacrylate copolymer with dimethyl sulfate. Suitable neutralizers include amino methyl propanol, etc. Suitable plasticizers include ethyoxylated lanolin alcohols, $C_{12-15}$ alcohols benzoate, glycerine, etc. Suitable solvents include isopropyl alcohol, anhydrous ethanol, or mixtures thereof.

The compounds of Formula I, II, and III may also be added to other hair fixative type compositions such as aerosol hair sprays, hair setting lotions and styling aids. Suitable hair setting lotions contain about 0.01–10% of hair fixative, 0.01–5% plasticizer, 20–70% solvent, or mixtures thereof.

Suitable hair fixatives include polyvinylpyrrolidone vinyl acetate, polyquaternium compounds, polyvinylpyrrolidone, or mixtures thereof. Suitable plasticizers include glycerine, ethyoxylated lanolin alcohols, $C_{12-15}$ alcohols benzoate, etc. Suitable solvents include methylene chloride, isopropyl alcohol, anhydrous ethanol or mixtures thereof.

The compounds of Formula I, II, and III may also be incorporated into mousse compositions. Suitable mousse compositions contain 0.1-10% of hair fixative, 0.1-5% conditioner, 0.05-5% foaming agent, and 1-50% solvent. The hair fixatives, conditioners and foaming agents are as mentioned herein. Suitable foaming agents include octoxynol, etc.

The invention will be further described in connection with the following examples which are set forth for the purposes of illustration only.

EXAMPLE 1

A hair spritzer was made according to the following formula:

|  | w/w % |
|---|---|
| SD alcohol 40 B | 80.00 |
| AMP | 0.71 |
| Resin 28-2930 | 5.00 |
| Amphomer | 1.5 |
| Dimethicone copolyol | 0.30 |
| Silk Protein | 0.10 |
| Cocamidopropyl Betaine | 0.10 |
| Water qs | |
| Fragrance | 0.30 |
| Methoxypropylgluconamide | 0.10 |
| Benzophenone 3 | 0.30 |

EXAMPLE 2

A hair styling gel was made as follows:

|  | w/w % |
|---|---|
| Water | 74.21 |
| Carbomer 940 | 17.00 |
| Water | 2.00 |
| PVPK-30 | 4.80 |
| Triethanolamine | 0.60 |
| Kathon CG | 0.04 |
| DMDM Hydantoin | 0.40 |
| PEG-75 Lanolin | 0.50 |
| PEG-75 Lanolin | 0.50 |
| Fragrance | 0.03 |
| Methyl paraben | 0.10 |
| PEG 40 hydrogenated Castor Oil | 0.30 |
| Hydrolyzed Silk | 0.10 |
| Panthenol | 0.10 |
| Benzophenone 4 | 0.05 |
| Methoxypropylgluconamide | 0.10 |

EXAMPLE 3

A shampoo for dry and damaged hair was made as follows:

|  | w/w % |
|---|---|
| Water | qs |
| Sodium Lauryl Ether Sulfate | 14.00 |
| Decyl Polyglucose | 14.00 |
| Lauramide DEA | 3.00 |
| Citric Acid | 0.05 |
| Methylparaben | 0.10 |
| Propylparaben | 0.05 |
| Guar Hydroxypropyltrimonium Chloride | 0.30 |
| Water | 10.00 |
| Glycol Stearate | 1.70 |
| Myristic Acid | 0.20 |

|  | w/w % |
|---|---|
| Sodium Lauryl Ether Sulfate | 10.00 |
| Dimethicone Copolyol | 0.20 |
| Glycerin | 0.20 |
| Trisodium HEDTA | 0.23 |
| Methoxypropylgluconamide | 0.25 |
| Kathon CG | 0.04 |

EXAMPLE 4

A hair fixative gel was made as follows:

|  | w/w % |
|---|---|
| Water | qs |
| Polyvinylpyrrolidone | 4.00 |
| Hydrolyzed Silk Protein | 0.10 |
| Water | 35.00 |
| Propylene Glycol | 0.30 |
| Methylparaben | 0.10 |
| Polyquat 11 | 1.00 |
| Polysorbate 20 | 0.50 |
| Kathon CG | 0.04 |
| Fragrance | 0.30 |
| Methoxypropylgluconamide | 0.0001 |

EXAMPLE 5

A hair conditioner was made as follows:

|  | w/w % |
|---|---|
| Water | 72.18 |
| Polyvinylpyrrolidone | 1.00 |
| Propylene glycol | 2.00 |
| Dicetylcimonium chloride | 1.00 |
| Octylmethoxy cinnamate | 0.01 |
| Hydroxyethyl cellulose | 1.25 |
| Fragrance | 0.60 |
| Water | 20.00 |
| Cetyl alcohol | 0.50 |
| Stearamido propyl stearamine | 0.50 |
| ceatearyl alcohol/ceteareth 20 | 2.00 |
| Propyl paraben | 0.02 |
| Methyl paraben | 0.10 |
| Methoxypropyl gluconamide (50%) | 0.25 |
| Hydrolyzed Silk | 0.10 |
| Kathon CG | 0.04 |

EXAMPLE 6

An aerosol hair spray was prepared according to the following formula:

|  | w/w % |
|---|---|
| SD 40B alcohol | QS |
| AMP | 0.60 |
| Vinyl acetate crotonic acid copolymer | 5.000 |
| Vinyl neodecanoate | |
| Polysorbate 80 | 0.200 |
| Polysorbate 20, acetylated alcohol | 0.100 |
| PPG-20 Methyl glucose ether | 0.070 |
| Fragrance | 0.200 |
| Ethyl ester of hydrolyzed silk | 0.100 |
| Methoxypropyl gluconamide | 0.050 |

About 70 parts of the above mixture was mixed with about 17 parts Dymel 152A and 13 parts of Hydrocarbon A17.

EXAMPLE 7

An aerosol hairspray was made as follows:

| | w/w % |
|---|---|
| SD 40B alcohol | QS |
| AMP | 0.65 |
| Vinyl acetate/crotonic acid vinyl neodecanoate copolymer | 7.00 |
| Fragrance | 0.20 |
| Ethyl ester of hydrolyzed silk | 0.10 |
| Water | 25.00 |
| Cyclomethicone | 0.10 |
| Methoxypropylgluconamide | 0.05 |

About 70 parts of the above formulation was mixed with 10 parts of Hydrocarbon A31 and 20 parts of Dymel A.

EXAMPLE 8

A shaving foam was made as follows:

| | w/w % |
|---|---|
| Water | QS |
| Methylparaben | 0.20 |
| GLycerin | 8.00 |
| Allantoin | 0.25 |
| PVP | 0.25 |
| Dioctyl sodium sulfosuccinate | 1.00 |
| TEA (98%) | 3.70 |
| Palmitic acid | 6.00 |
| Stearic acid | 2.00 |
| Propylparaben | 0.10 |
| Lanolin oil | 0.30 |
| BHT | 0.01 |
| Jojoba oil | 1.50 |
| Water | 2.00 |
| Fragrance | 1.00 |
| Methoxypropylgluconamide | 0.50 |

About 96 parts of the above formulation was mixed with 4 parts of hydrocarbon propellant.

EXAMPLE 9

A shaving gel was made as follows:

| | w/w % |
|---|---|
| Water | QS |
| FD&C Blue #1 | QS |
| Hydroxypropylcellulose | 0.15 |
| Sorbitol | 6.00 |
| Triethanolamine (98%) | 8.00 |
| Palmitic acid | 10.00 |
| Propylene glycol isostearate | 3.00 |
| Fragrance | 0.50 |
| Methoxypropylgluconamide | 0.50 |

About 96 parts of the above formulation was mixed with 4 parts of hydrocarbon propellant.

EXAMPLE 10

A brushless shave cream was made as follows:

| | w/w % |
|---|---|
| Water | QS |
| Polyquaternium 10 | 0.05 |
| PEG 14M | 0.20 |
| Butylene glycol | 2.50 |
| Glycerin | 3.00 |
| Cocamido propyl betaine | 4.00 |
| Methyl paraben | 0.35 |
| Propyl paraben | 0.20 |
| Stearic acid | 16.00 |
| Glycol stearate | 2.00 |

-continued

| | w/w % |
|---|---|
| Phenyl trimethicone | 2.50 |
| Dimethicone | 1.00 |
| Sorbitan laurate | 0.50 |
| Polysorbate 20 | 2.00 |
| Lanolin, isopropyl lanolate | 7.00 |
| TEA (98%) | 1.60 |
| Fragrance | 0.50 |
| Methoxypropylgluconamide | 0.50 |

EXAMPLE 11

Figure 2:
FIG. 2: is a photograph at 5000X magnification of a brown hair tress which was shampooed ten times with a standard shampoo composition without methoxypropylgluconamide. The tress does not show any build up of material on and between the cuticle layers as is seen on the tress in FIG. 1.
Figure 3:
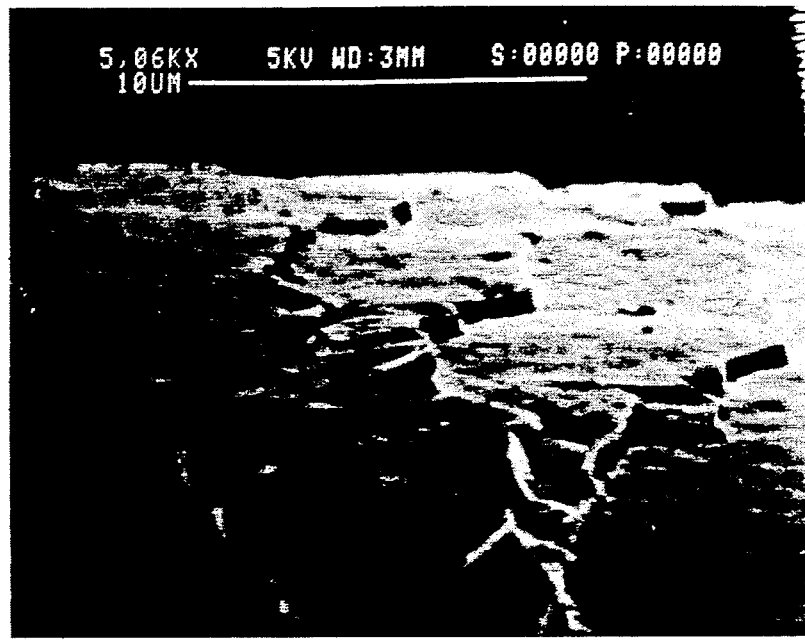
FIG. 3: is a photograph at 5000X magnification of a brown hair tress which was shampooed one time with a standard shampoo composition containing 5% methoxypropylgluconamide. A slight build up of material on and between the hair cuticle is seen.
Figure 4:
FIG. 4: is a photograph at 5000X magnification of a brown hair tress which was shampooed one time with a standard shampoo composition without methoxypropylgluconamide. No build up of material is seen on the cuticle.
Figure 5:
FIG. 5: is a photograph at 5000X magnification of a bleached hair tress which was shampooed ten times with a standard shampoo composition containing 5% methoxypropylgluconamide. A significant build up of material on and between the cuticles is evident.
Figure 6:
FIG. 6: is a photograph at 5000X magnification of a bleached hair tress which was shampooed ten times with a standard shampoo composition without methoxypropylgluconamide. No build up on and between the cuticles is seen in contrast to FIG. 5.
Figure 7:
FIG. 7 is a photograph at 5000X magnification of a bleached hair tress which was shampooed one time with a standard shampoo composition containing 5% methoxypropylgluconamide. A slight build up of material is seen on and between the cuticles.
Figure 8:
FIG. 8: is a photograph at 5000X magnification of a bleached hair tress which was shampooed one time with a standard shampoo composition without methoxypropylgluconamide. In contrast to FIG. 7, no build up of material is seen on and between the cuticles.

Brown and bleached hair tresses were washed one time and ten times with a shampoo composition alone, and a shampoo composition to which 5% methoxypropylgluconamide was added. The tresses were observed under the microscope at 5000X magnification. As illustrated in FIGS. 1-8 supra, the tresses shampooed ten times with shampoo containing 5% methoxypropylgluconamide exhibited a significant build up of material on the hair cuticle as compared to the hair tresses shampooed ten times with the same shampoo composition without methoxypropylgluconamide. Even the bleached and brown hair tresses which were shampooed only once with shampoo containing 5% methoxypropylgluconamide exhibited a build up of material which was not seen in the hair tresses shampooed with the same shampoo composition without methoxypropylgluconamide.

While the invention has been described in connection with the preferred embodiments it is intended to cover alternatives, modifications, and equivalents as may be included within the spirit and scope of the invention as defined by the appended claims.

What is claimed is:

1. A hair care composition selected from the group consisting of a shampoo composition comprising 1-45% anionic surfactant, 1-55% water and 0.01-10% of a foam booster selected from the group consisting of cocamide MEA, cocamide DEA, lauramide DEA, capramide DEA, cetearyl alcohol, cetyl alcohol, cetyl betaine, cocamide MIPA, cocamidoethyl betaine, cocamidopropylamine oxide, cocamidopropyl betaine, cocamidopropyl hydroxysultaine, cocamide oxide, coconut alcohol, coco-sultaine, lauryl betaine, lauryl sultaine, lauryl alcohol, myristamide DEA, myristamide MEA, oleyl betaine, sodium sarcosinates, potassium coco-hydrolyzed silk protein, and mixture thereof, a conditioner composition comprising 10-95% water, 1.0-10% of a cationic polymer selected from the group consisting of cetyl trimethyl ammonium chloride, stearylamidopropylethyldimonium ethosulfate, Polyquaternium 11, oleylamidopropyl amine oxide, guar hydroxypropyl trimonium chloride, trimethylsilylamodimethicone, stearyl dimethyl benzyl ammonium chloride, cetyl pyridinium chloride, dicetyl dimethyl ammonium chloride and mixtures thereof, and 0.1-10% conditioning agent, a hair spray composition comprising 0.001-10% of a resin selected from the group consisting of vinyl acetate/crotonic acid/vinyl neodecanoate copolymer, octylacrylamide/acrylates/-butylamino ethylmethacrylate copolymer, vinyl acetate/crotonic acid, polyvinylpyrollidone, polyvinyl pyrollidone vinyl acetate copolymer, PVP acrylates copolymer, the ethyl ester of polyvinyl methylether/-maleic anhydride, polyvinylpyrrolidone acetate, polymeric quaternary ammonium salts prepared by the reaction of ethyl methacrylate/abietylmethacrylate/diethylamino ethyl methacrylate copolymer with dimethyl sulfate, a polymeric quaternary ammonium salt prepared by the reaction of ethyl methacrylate/oleylmethacrylate/diethylamino ethyl methacrylate copolymer with dimethyl sulfate and mixtures thereof, 0.01–5% neutralizer, 0.01–5% plasticizer, and 15–40% solvent, a hair setting lotion comprising 0.01–10% of a hair fixative resin selected from the group consisting of polyvinylpyrrolidone, vinyl acetate, polyquaternium compounds, polyvinylpyrrolidone, and mixtures thereof, 0.01–5% plasticizer, and 20–70% solvent, and a mousse composition comprising 0.1–10% of a hair fixative resin selected from the group consisting of polyvinylyrrolidone, vinyl acetate, polyquaternium compounds, polyvinylpyrrolidone, and mixtures thereof, 0.1–5% conditioner, 0.05–5% foaming agent, and 1–50% solvent, and comprising 0.001–10% of a compound of the formula (Formula I):

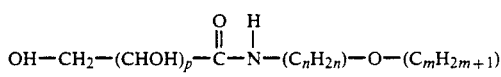

wherein p is a whole number from 1 to about 4, $(C_nH_{2n})$ is a straight or branched chain alkyl bridge in which n is a whole number of 1 to about 6, and $(C_mH_{2m+1})$ is a straight or branched chain alkyl radical in which m is a whole number of 1 to about 6.

2. The composition of claim 1 which is a shampoo.

3. The composition of claim 2 comprising 1–45% anionic surfactant, 1–55% water, and an ingredient selected from the group consisting of 0.01–10% thickener, 0.001–1% preservative, 0.001–1% chelating agent, or mixtures thereof.

4. The composition of claim 3 comprising 1–45% anionic surfactant, 1–55% water, 0.01–10% foam booster, 0.01–10% thickener, 0.001–1% preservative, 0.001–1% chelating agent.

5. The composition of claim 4 comprising 0.01–5% of the Formula I compound wherein p is a whole number from 1 to 4, $(C_nH_{2n})$ is a straight or branched chain alkyl bridge in which n is a whole number of 1 to 4, and $(C_mH_{2n+1})$ is a straight or branched chain alkyl radical in which m is a whole number of 1 to 4.

6. The composition of claim 4 comprising 0.01–5% of the Formula I compound wherein p is 4, n is 3, and m is 1.

7. The composition of claim 1 which is a conditioner.

8. The composition of claim 7 comprising 10–95% water, 1.0–10% cationic polymer, 0.1–10% conditioning agent, and an ingredient selected from the group consisting of 0.01–5% emulsifier, 0.01–5% emulsifier, 0.01–5% thickener, 0.001–1% acidulant, or mixtures thereof.

9. The composition of claim 8 comprising 0.01–5% of the compound of Formula I wherein p is a whole number from 1 to 4, $(C_nH_{2n})$ is a straight or branched chain alkyl bridge in which n is a whole number of 1 to about 4, $(C_mH_{2m+1})$ is a straight or branched chain alkyl radical in which m is a whole number of 1 to about 4.

10. The composition of claim 9 comprising 0.01–5% of the compound of Formula I wherein p is 4, n is 3, and m is 1.

11. The composition of claim 1 which is a hair spray.

12. The composition of claim 11 additionally comprising 15–60% propellant.

13. The composition of claim 12 comprising 0.01–5% of the compound of Formula I wherein p is a whole number from 1 to 4, $(C_nH_{2n})$ is a straight or branched chain alkyl bridge in which n is a whole number of 1 to about 4, $(C_mH_{2m+1})$ is a straight or branched chain alkyl radical in which m is a whole number of 1 to about 4.

14. The composition of claim 13 comprising 0.01–5% of the compound of Formula I wherein p is 4, n is 3, and m is 1.

15. The composition of claim 1 which is a mousse.

* * * * *